(12) United States Patent
Bauer et al.

(10) Patent No.: US 9,445,982 B2
(45) Date of Patent: Sep. 20, 2016

(54) POLYMER-BASED PIGMENT-BEARING INK

(75) Inventors: Barbara Bauer, Burgkirchen a. d. Alz (DE); Karin Hofmann, Lauf (DE)

(73) Assignee: Schwan-STABILO Cosmetics GmbH & Co. KG, Heroldsberg (DE)

(*) Notice: Subject to any disclaimer, the term of this patent is extended or adjusted under 35 U.S.C. 154(b) by 229 days.

(21) Appl. No.: 12/124,194

(22) Filed: May 21, 2008

(65) Prior Publication Data

US 2008/0292570 A1 Nov. 27, 2008

(30) Foreign Application Priority Data

May 25, 2007 (DE) .................. 20 2007 007 455

(51) Int. Cl.
*A61K 8/81* (2006.01)
*A61Q 1/10* (2006.01)
*A61K 8/86* (2006.01)

(52) U.S. Cl.
CPC ............... *A61K 8/8152* (2013.01); *A61K 8/86* (2013.01); *A61Q 1/10* (2013.01); *A61K 2800/43* (2013.01)

(58) Field of Classification Search
CPC .. A61K 8/8152; A61K 8/86; A61K 2800/43; A61Q 1/10
USPC ........................................ 424/63, 70.6, 78.03
See application file for complete search history.

(56) References Cited

U.S. PATENT DOCUMENTS

| | | | | |
|---|---|---|---|---|
| 4,988,502 | A * | 1/1991 | Ounanian et al. ............... 424/63 |
| 5,593,680 | A * | 1/1997 | Bara et al. .................... 424/401 |
| 5,645,609 | A * | 7/1997 | Andrean et al. .................. 8/405 |
| 5,800,825 | A * | 9/1998 | McMullen .................... 424/401 |
| 5,874,072 | A * | 2/1999 | Alwattari et al. ............. 424/70.7 |
| 6,010,686 | A | 1/2000 | De La Poterie et al. |
| 6,024,968 | A * | 2/2000 | Suess et al. .................. 424/401 |
| 6,106,820 | A * | 8/2000 | Morrissey et al. ......... 424/78.18 |
| 6,517,823 | B1 | 2/2003 | Norman et al. |
| 7,008,994 | B1 * | 3/2006 | Waki .............................. 524/556 |
| 2002/0034480 | A1 | 3/2002 | Grimm et al. |
| 2003/0021817 | A1 | 1/2003 | Arnaud-Sebillotte et al. |
| 2004/0223935 | A1 | 11/2004 | Meunier |
| 2004/0234486 | A1 | 11/2004 | Hashimoto |
| 2004/0265258 | A1 * | 12/2004 | Robinson et al. .......... 424/70.12 |
| 2005/0002881 | A1 * | 1/2005 | Aota ............................... 424/63 |
| 2005/0129639 | A1 | 6/2005 | Quemin |
| 2005/0163741 | A1 * | 7/2005 | Zech ........................... 424/70.16 |
| 2006/0078520 | A1 | 4/2006 | Pays et al. |
| 2006/0104936 | A1 * | 5/2006 | Pays et al. .................. 424/70.16 |
| 2006/0140984 | A1 * | 6/2006 | Tamarkin et al. ............. 424/400 |
| 2006/0257342 | A1 * | 11/2006 | Mu et al. ......................... 424/63 |
| 2008/0199415 | A1 * | 8/2008 | Feng et al. ....................... 424/69 |

FOREIGN PATENT DOCUMENTS

| | | |
|---|---|---|
| DE | 20009445 | 8/2000 |
| EP | 1077062 | 2/2001 |
| EP | 1462084 | 9/2004 |
| EP | 1529513 | 5/2005 |
| FR | 2844192 | 3/2004 |
| JP | 54049338 A | 4/1979 |
| JP | 54151139 A | 11/1979 |
| JP | 06239718 A | 8/1994 |
| JP | 10-231233 | 9/1998 |
| JP | 11189513 A | 7/1999 |
| JP | 2001328921 A | 11/2001 |
| JP | 2003012447 A | 1/2003 |
| JP | 2003521489 A | 7/2003 |
| JP | 2004339108 | 12/2004 |
| JP | 2005330222 A | 12/2005 |
| WO | WO 2008/14528 A1 * | 12/2008 |

OTHER PUBLICATIONS

About.com Chemistry, Solutions, Suspensions, Colloids, and Dispersions [Downloaded Jul. 7, 2011] [Retrieved from internet <URL: http://chemistry.about.com/od/lecturenotes13/1/colloids.htm?p=1 >], 1 page.*
The Free Online Dictionary, Colloidal dispersion—definition [Downloaded Jul. 7, 2011] [Retrieved from internet <URL: http://www.thefreedictionary.com/Colloidal+dispersion >], 3 pages.*
International Preliminary Report on Patentability, PCT/EP2008/003874 (Bauer et al., WO 2008/14528 A1), issued Dec. 1, 2009; 7 pages.*
Machine translation of JP 2005-330222 A. Translated on Jul. 18, 2013.*
Interpolymer Corporation. "Syntran PC 5100." Retrieved Jul. 18, 2013. Retrieved from the internet <URL: http://www.interpolymer.com/contentmgr/showdetails.php/id/939>.*
Lochhead (2007). "Chapter 1: The Role of Polymers in Cosmetics: Recent Trends." [retrieved on Apr. 10, 2015]. Retrieved from the internet <URL:http://pubs.acs.org/doi/pdf/10.1021/bk-2007-0961.ch001>.*

* cited by examiner

*Primary Examiner* — Brian-Yong Kwon
*Assistant Examiner* — Doan Phan
(74) *Attorney, Agent, or Firm* — Bachman & LaPointe, PC

(57) ABSTRACT

A cosmetic water-based ink containing at least one acryl-based polymer, at least one polymeric ionic thickener, at least one anionic or amphoteric-ionic surfactant, at least one material in particle form and at least one non-ionic surfactant, wherein the non-ionic surfactant is a compound which contains between 4 and 8 units of PEG or PPG and a $C_6$-$C_{20}$ fatty acid residue.

20 Claims, No Drawings

POLYMER-BASED PIGMENT-BEARING INK

BACKGROUND OF THE INVENTION

The invention relates to a colored aqueous polymer-based ink for use on the skin and/or the mucous membranes.

Generally coloring systems on a solvent basis are referred to as inks. They are generally dispersed systems of a suspension character, which as main components contain a solvent and a coloring agent, in particular a pigment and/or a dyestuff. In addition they may contain further ingredients such as polymers, stabilisers and dissolution aids and other additives for imparting special properties. An area of use for coloring aqueous inks is the field of decorative cosmetics where inks could be used in many forms inter alia for makeup, mascara, eyeliner and lipliner and eyebrow texturing agents.

If inks are to be used for a cosmetic application they must comply with the requirements to be imposed on cosmetic compositions. Thus they should be as easy to apply as possible. Upon one-off application, it should be possible to achieve a rich full application of color without having to put on too much material. Rapid drying is desirable so that the ink does not run and cannot form drips. Particularly in the eye region, the aim is also to avoid what is referred to as 'touch-up', which means the material coming off after having been applied as eyeliner to the upper eyelid due to the eye being opened. After drying the material should have good durability, be water-resistant and, in the case of eye cosmetics, it should also be tears-resistant, it should be transfer-resistant, that is to say it should not come off on to other surfaces and articles, and it should not migrate or bleed out of the region in which it was applied. Furthermore the applied ink should be resistant to being rubbed with the fingers and should not lead to cracking or tautness effects, in particular when using an eyeliner ink which is to be applied to the eyelid. Further demands on inks of that kind concern the effect to be achieved. Thus the application is to be shiny and intensive in color and the film formed is to be elastic and only adhesive in relation to the skin while the surface is to be smooth and non-sticky or greasy.

Admittedly, the field of cosmetics already involves the use of inks, the properties of which however are still not satisfactory. Thus, there are problems with the known inks insofar as the pigments settle upon storage over a prolonged period. In addition the application properties are not satisfactory and the durability of the applied films is inadequate. The previously known inks are frequently systems based on oil or silicone or are emulsions. Oil-based or silicone-based systems suffer from the disadvantage that, because of the lipophilia of the raw materials, the mass is admittedly well distributed on the skin but has a tendency to migration which is promoted by the skin grease. After having been worn for a period of some hours the material has a tendency to migrate into wrinkles.

In order to improve silicone-based inks in regard to migration, it has already been proposed that silicone resins may be added. Corresponding systems actually adhere to the place of application for longer, but due to the severe tendency on the part of the resin for film formation unpleasant tautness feelings however occur, which is highly disadvantageous in particular when applied to the eyelids.

In addition there have already long been cosmetic inks on an emulsion basis, which are generally in the form of O/W emulsions. Emulsions are preferred in the state of the art by virtue of their lesser tendency to settlement. On the one hand the pigments can bind elements by virtue of their both lipophilic and also hydrophilic character in both phases and thereby hold them in suspension. On the other hand viscosity is generally increased, which also stabilises pigments in their suspended condition. The advantage of the improved ink stability is however counteracted by losses in terms of the application properties and the durability of the applied ink. Cosmetic emulsion-based inks are generally viscous, transfer too much material on to the skin and therefore lead to the touch-up phenomenon. Furthermore they also have a tendency to migrate into skin wrinkles and to bleed out by virtue of the lipophilic character of the oil phase.

US-A 2006/00078520 discloses water-resistant cosmetic compositions for hair care, which are in the form of an aqueous dispersion. Those compositions contain at least one polymer dispersion, a polymer electrolyte and a surfactant with an HLB of 6 or more. Those compositions further also include a wax for structuring purposes. Wax has already long been used for structuring cosmetic materials. Wax however contributes to the touch-up phenomenon and is therefore disadvantageous in particular when used on lips or eyelids.

In addition WO 02/056853 describes a cosmetic composition in which iridescent constituents are held in dispersion by a gel form. Such a gel however is not suitable for eyeliners or lipliners.

A water-based, polymer-bearing composition is also described in EP 0 793 957. In that case the polymers are intended to improve the durability of the applied materials without at the same time giving rise to unpleasant tautness effects. The described rudimentary formulations which only consist of polymer, water, pigment and a softener, for example glycerin, can however only enhance the durability of cosmetic inks in the area of application. Aesthetic aspects such as sheen and mechanical aspects such as water-resistance and rubbing-resistance with at the same time ease of application with a full rich application of color are not taken into consideration in that respect. Furthermore, in regard to the compositions known from that document, the stability of the material in regard to temperature storage and prolonged period of use is disregarded. Those properties however play a large part in terms of a marketable product.

Now, taking that state of the art as its basic starting point, the object of the present invention is to overcome the above-described disadvantages of the known pigmented inks and to provide a product for decorative cosmetics, which combines good application properties with improved adhesion and aesthetic properties. A further object was to provide a product which is water-resistant, which does not smudge, which does not migrate into wrinkles, which has sheen and which adheres for a long time to the place of application. Furthermore the invention aims to provide a product which even under prolonged storage can be completely re-dispersed again and can always still be well applied.

SUMMARY OF THE INVENTION

The specified objects are obtained by providing a composition according to the present invention which is a stable product which can be stored over a long period and which can be well applied is achieved by a well-matched combination of polymers, dispersing and thickening agents in an aqueous system.

DETAILED DESCRIPTION

The invention provides a cosmetic water-based ink composition which contains at least one acryl-based polymer, at least one polymeric ionic thickener, at least one anionic or amphoteric-ionic surfactant and at least one non-ionic surfactant, as well as a substance in particle form, wherein the non-ionic surfactant is a compound which contains between 4 and 8 units of PEG or PPG and a $C_6$-$C_{20}$ fatty acid residue.

It was surprisingly found that, when using that combination of at least five components, the result achieved is a highly stable homogeneous composition which combines a high level of stability with excellent application properties and very good adhesion at the place of application. Furthermore, when using the combination according to the invention it is possible to dispense with lipid-bearing systems and oil components, which overcomes the problems with migration and smearing and smudging and at the same time provides a product which can be very well applied. Furthermore the water resistance of the composition according to the invention is extremely high. After application the product dries to give a film which shines and has a highly aesthetic appearance. Such a combination of properties could not be achieved with the previously known ink compositions which were used in cosmetics.

The system according to the invention is a dispersion with a suspension character, in which the constituents in particle form are contained in finely divided form as a continuous phase in water. The rheology of the suspension is influenced by the further ingredients in such a way that the particulate ingredients are prevented from settling. The rheological-modifying agent used according to the invention increases the viscosity of the material and thus reduces the mobility of the particles of higher density, with the effect that the particles already remain distributed homogeneously in the medium for physical reasons. In addition the rheology-modifying agent also contributes chemically to stabilisation as it can hold the particles in a suspended condition by virtue of constructive interaction. Even if the particles have settled after a prolonged storage time by virtue of their natural high density, they can be easily homogeneously distributed again by shaking them afresh, by virtue of the dispersion-promoting agents contained in accordance with the invention.

Without being tied down to a theory, it can be assumed that the PEG-bearing surfactant and the thickener provide for stabilisation of the particulate ingredient in the aqueous phase while the ionic surfactant which can be anionic or amphoteric-ionic provides for good applicability and adhesion by a reduction in surface tension.

The composition according to the invention is in the form of a suspension, wherein the solvent or solvents or suspension agent or agents or the continuous phase are based on water, that is to say water or a mixture of water and one or more water-soluble solvents forms the continuous phase. Preferably pure water is used as the continuous phase or solvent.

The composition according to the invention is suitable for any water-based ink. Advantages are achieved if a particulate ingredient is included. The combination according to the invention is particularly advantageous for pigment-bearing mixtures, that is to say cosmetic compositions which as coloring agents use one or more pigments or also mixtures of pigments with soluble dyestuffs and optionally stabilisers. An ink with advantageous properties is also achieved when the coloring agents are all soluble dyestuffs so that this embodiment is also considered in accordance with the invention.

All substances in powder or particle form which are usually known in cosmetics can be used as the particulate ingredient which is one of the components according to the invention. The only condition placed on the substances is sufficiently low toxicity as the ink is applied to the skin or mucous membrane.

The above-mentioned solid or particulate substance includes ingredients in particle form which are not dissolved in the continuous phase. The phase in particle form can comprise for example fillers such as for example talc, kaolin, starch and modified starch, polytetrafluoroethylene powder (Teflon), nylon powder, boron nitride, insoluble metal soaps such as Mg stearate, Ca stearate, Sr stearate, Zn stearate, effect materials such as spangles, glitter, fluorescent and phosphorescent particles and in particular inorganic or organic pigments or mixtures of said substances.

The following can be mentioned as pigments by way of example: titanium dioxide, zinc oxide, iron oxides, chromium oxide, chromium hydroxide, ultramarine, Berlin Blue (Ferric Blue), mica, pearlescent agents such as for example titanium dioxide-coated micas, colored micas coated with titanium dioxide and metal oxides, bismuth oxychloride, coated bismuth oxychloride, flake metal powder of aluminum, brass, bronze, copper, silver, gold and lakes of organic coloring agents with aluminum, barium, zirconium, calcium or strontium. That list is only by way of example and is not conclusive.

If desired it is also possible to use as sun protection agents particularly finely divided pigments, referred to as nanopigments, involving a mean particle size of between 5 and 50 nm, which act transparently on the skin and no longer color it. Mention may be made by way of example here of silicon dioxide, titanium dioxide, cerium oxide, aluminum oxide, zirconium oxide and zinc oxide.

In a preferred embodiment lakes of organic dyestuffs are used as coloring agents. It has been found that the combination of lakes of organic dyestuffs with the suspension according to the invention provides that the dyestuffs do not bleed out but remain in the structure produced.

The composition according to the invention may also contain pearlescent pigments and metal powders in leaf form alone or in addition to pigments.

The amount of the particulate substances used corresponds to the amounts usually employed in cosmetics, preferably the amounts are so adjusted that they range within the limits of the highest amounts allowed by the respective cosmetic legislation. The combination according to the invention of components, which provides a high stabilisation effect, permits a very high proportion of ingredients in particle form. If just a soft coloring effect or a low level of action is desired, the proportion of constituents in particle form however can also be very low. A very wide range in regard to the amount of that ingredient is therefore considered, which may be only 0.1% by weight if little or no coloring is wanted, but which can also be 50% by weight or more if a full rich shade is to be achieved on the skin. Usually amounts in the range of between 5 and 30% by weight, preferably between 8 and 20% by weight are used. For pigments as the materials in particle form, amounts in the range of between 10 and 16% by weight have been found to be particularly advantageous. All percentages in this description refer to weight and in general to the weight of the overall composition unless otherwise stated or if the context indicates otherwise.

As stated above excellent properties are achieved when the cosmetic ink contains special surfactants and thickeners which produce a stabilising matrix.

A non-ionic surfactant with polyethylene oxide or polypropylene oxide components and a fatty acid component which contains between 6 and 20 and preferably between 8 and 16 C-atoms is used as the stabilising component which is essential according to the invention. The proportion of the PEG or PPG units is in a range of between 4 and 8. Shorter chains cannot achieve the desired effect while longer chains make the surfactant excessively hydrophobic.

Preferably non-ionic surfactants are used, which have between 4 and 8 PEG units. The fatty acid component is preferably selected from caprylates, caprinates, lanolates, laurates, olivates, coconut oil acids and mixtures thereof.

Furthermore the compounds may additionally contain a glyceryl residue. The fatty acids used can be saturated or unsaturated, saturated fatty acids being preferred by virtue of the better resistance. The following surfactants have proven to be particularly suitable: PEG-6 caprylic/capric glycerides, PEG-4 castor oil, PEG-4 dilaurate, PEG-4 lanolate, PEG-4 laurate, PEG-4 olivate, corn oil PEG-6 esters and PEG-6 carylate/caprate.

The non-ionic surfactant should be contained in the composition in an amount of at least 0.2 and not more than 3% by weight. A proportion of more than 3% by weight is unwanted as non-ionic surfactants have a certain irritation potential. A proportion below 0.2% by weight generally does not afford the desired effect. A proportion of between 0.3 and 1% by weight is preferably used.

By virtue of its structure on the one hand the non-ionic surfactant has a strong polar character which is contributed by the ethoxy group and on the other hand a lipophilic component which is contributed by the alkyl residue of the fatty acid. In that way the non-ionic surfactant performs a number of functions, namely reducing the surface tension of the water, solution-aiding properties by way of the alkyl component and thus leads to good wetting of the skin and homogeneous distribution in the aqueous medium.

In order further to improve the applicability the surface tension of the aqueous solution is reduced by employing at least one polymeric ionic surfactant which can be anionic or amphoteric-ionic. It was found that the combination of an anionic or amphoteric-ionic and a non-ionic surfactant imparts enhanced stability to the system. The combination increases the dispersibility of the polymer in the material so that its tendency to gel or separate out into flakes is suppressed and the soluble component of the polymer can be increased. The use of the two kinds of surfactants therefore leads to the material having a particularly advantageous structure.

Examples of anionic or amphoteric-anionic surfactants that can be mentioned are sulfosuccinate, sodium polystyrene sulfonate, sodium cocoyl apple amino acids, Cco hydroxyl sultaine, potassium dihydroxyethyl cocamine oxide phosphate, dimethicone propyl PG-betaine and amphodiacetate. As the ink according to the invention is applied to skin and mucous membrane, it is preferable to use only those ionic surfactants, whose irritation potential is sufficiently low and which are allowed for that purpose.

The anionic or amphoteric-anionic surfactant is employed in the amounts which are usually used, a proportion of between 0.2 and 3% by weight has been found to be suitable, with a proportion of 0.3 to 1% by weight being preferred.

A further important constituent of the composition according to the invention is at least one polymer. The use of polymers is known in the field of cosmetics. Both water-soluble and also water-dispersible polymers are used in cosmetics, in particular for lipsticks. Polyvinyl alcohols or polyvinyl pyrrolidones which are water-soluble and which can therefore be easily processed are popular. It was however now surprisingly found that lipophilically modified polymers on an acrylate base are particularly well suited to being added to an ink which can be applied to the skin. They have excellent adhesion to the skin, thereby providing for good durability of the applied material with a high level of water resistance on the applied surface. By virtue of the acrylate component in combination with suitable stabilisers and dissolution aids, they have very good water solubility or water dispersibility so that they can be homogeneously distributed in the composition. Preferably alkyl, alkaryl or aryl-substituted acrylate copolymers are used, which can be added to the composition either in the form of an aqueous or ethanolic dispersion or also in powder form. If the composition which contains the polymer or polymers is applied to the surface of the skin, an elastic film is formed, in which the non-volatile raw materials of the formulation and in particular the pigments are permanently homogeneously embedded and thus ensure invariable high durability, which remains at the same level, of the material on the applied surface. The polymer is jointly responsible for the structure which is formed in the ink and which permanently stabilises the further ingredients, in particular constituents in particle form.

Preferably the polymers used are those which are produced by radical polymerisation or a condensation reaction. These include inter alia acrylate copolymers such as acrylates/ethylhexyl acrylate/styrene copolymers, acrylates/ethylhexyl acrylate/HEMA/styrene copolymer, acrylates/hydroxyesters acrylates copolymer, acrylates/lauryl acrylate/stearyl acrylate/ethylamine oxide methacrylate copolymer, acrylates/octylacrylamide copolymer, butyl acrylate/ethylhexyl methacrylate copolymer, butyl acrylate/styrene copolymer and styrene/acrylates/ammonium methacrylate copolymer.

By virtue of the special combination of components it is possible to add a high proportion of polymers to the composition according to the invention. The polymer can be stably included in the composition up to a proportion of 70% by weight or even more. Preferably the polymer is used in a proportion of between 20 and 70% by weight and particularly preferably between 40 and 60% by weight. If the concentration is below 20% the desired sheen, the very good durability and the water resistance cannot always be achieved. A concentration of over 70% by weight can give rise to incompatibility in the material and in addition can form an excessively viscous material due to gelling of the polymer.

As a further component which is essential to the invention the ink according to the invention contains a polymeric, ionic rheology-modifying agent. It was surprisingly found that the rheology-modifying agent not only increases the viscosity of the composition but that agent also, in combination with the non-ionic surfactant, becomes attached to the surface of the constituents in particle form and holds them in suspension. That synergistic co-operation provides for high stabilisation of the composition.

The pigments, for example inorganic oxides or organic lakes and micas, have rather a polar character. Particularly in combination with the non-ionic surfactant they form polar locations on the surface. A constructive interaction occurs with those locations between the polymer thickener and the pigments. Individual molecule constituents are permanently accumulated on the surface of the pigments, partially enclose them and are thus also distributed homogeneously in the material.

The composition can additionally contain polymeric thickening agents. The following may be named as examples of polymeric thickening agents according to the invention: acrylamide/ethalkonium chloride acrylate copolymer, acrylates/C10-30 alkyl acrylate crosspolymer, acrylates/methacrylate copolymer, ammonium acrylates copolymer, calcium carrageenan, cabomer, hydroxypropyl starch phosphate, sodium acrylates copolymer, sodium polyacrylate and sodium polystyrene sulfonate. Preferably acrylic acid thickeners are used. The thickeners are used in the amounts which are usual for cosmetic compositions.

The preparation according to the invention may also contain additives which are usual in cosmetics such as preserving agents, moistening agents, perfumes, pH-regulators, aroma substances, anti-oxidants, odiferous substances, vitamins, sun protection filters, care agents and the like, in the amounts which are usual for such substances.

By virtue of its texture the ink according to the invention is highly suitable for being applied to mucous membranes and even to the particularly sensitive eyelids.

A further subject of the invention is therefore the use of the ink according to the invention as eyeliner or eyebrow liner.

The invention is further described by means of the following Examples. In the Examples all amounts are specified in proportions by weight.

EXAMPLE 1

Eyeliner

An eyeliner was produced from the following components (the raw materials are specified by the INCI names):

| | |
|---|---|
| Pigments | 15.00 |
| Aqua | 22.00 |
| Sodium methylparaben | 0.20 |
| Sodium propylparaben | 0.20 |
| Phenoxyethanol | 0.4 |
| Glycerin | 7.50 |
| Hydroxypropyl starch phosphate | 0.5 |
| Butyl acrylate/styrene copolymer | 50.20 |
| Sodium cocoyl apple amino acids | 0.9 |
| PEG-6 caprylate/caprate | 0.4 |
| Sorbitol | 1.2 |
| Bis-PEG/PPG-16/16 PEG/PPG 16/16 dimethicone | 1.5 |

All liquid constituents except for the polymer which in the present case was used in the form of a dispersion were combined and stirred until they were homogeneous. The pigments, the parabens and the thickener were then introduced with an increase in the stirring speed and stirred for 30 minutes until the result was a uniform lump-free material. To conclude the polymer was dripped into the pigmented ink with slow stirring and stirred for a further 30 minutes. The result obtained was a colored ink which upon application gave a shiny colored film with a rich full covering effect and which remained on the eyelid for longer than 10 hours without smudging.

EXAMPLE 2

Eyebrow Ink

An eyebrow ink was produced from the following components (the raw materials are specified by the INCI names):

| | |
|---|---|
| Pigments | 5.00 |
| Aqua | 41.40 |
| Imidazolidinyl urea | 0.30 |
| Phenoxyethanol | 0.2 |
| Butane-1,3-diol | 7.00 |
| Ammonium acrylates copolymer | 0.3 |
| Acrylates/ethylhexyl acrylate/styrene copolymer | 40.80 |
| Dimethicone propyl PG-betaine | 0.3 |
| PEG-4 laurate | 1.0 |
| Glycerin | 4.0 |

All liquid constituents except for the polymer which in the present case was used in the form of a dispersion were combined and stirred until they were homogeneous. The pigments, the parabens and the thickener were then introduced with an increase in the stirring speed and stirred for 30 minutes until the result was a uniform lump-free material. To conclude the polymer was dripped into the pigmented ink with slow stirring and stirred for a further 30 minutes. The result obtained was a discreetly coloring ink which by virtue of the sheen afforded imparts an intensive expression for the eye and which by virtue of its explicit application property harmonically copies the eyebrow portion.

EXAMPLE 3

Eyeliner

An eyeliner was produced from the following components (the raw materials are specified by the INCI names):

| | |
|---|---|
| Pigments | 16.00 |
| Aqua | 17.00 |
| Sodium methylparaben | 0.30 |
| Benzyl alcohol | 0.70 |
| Phenoxyethanol | 0.4 |
| Butane-1,3-diol | 7.40 |
| Sodium polyacrylate | 0.2 |
| Styrene/acrylate/ammonium methacrylate copolymer | 55.00 |
| Sodium cocoyl apple amino acids | 1.0 |
| PEG-6 caprylate/caprate | 0.2 |
| Sorbitol | 0.6 |
| Bis-PEG/PPG-16/16 PEG/PPG 16/16 dimethicone | 1.2 |

All liquid constituents except for the polymer which in the present case was used in the form of a dispersion were combined and stirred until they were homogeneous. The pigments, the parabens and the thickener were then introduced with an increase in the stirring speed and stirred for 30 minutes until the result was a uniform lump-free material. To conclude the polymer was dripped into the pigmented ink with slow stirring and stirred for a further 30 minutes. The result obtained was an eyeliner ink which when applied once remained unchanged for longer than 12 hours on the eyelid. The ink was well capable of flow, which afforded a homogeneous application of color to the part of the skin to which it was to be applied, and was nonetheless so quick-drying that it did not run, it did not form any drops or cause a touch-up.

The invention claimed is:
1. A water-based coloring cosmetic composition comprising at least one acryl-based polymer, at least one polymeric ionic thickener, at least one anionic or amphoteric-ionic surfactant, a particulate material, wherein the particulate material comprises a pigment and at least one non-ionic surfactant, wherein the non-ionic surfactant is a compound which contains between 4 and 8 units of PEG or PPG and a $C_8$ - $C_{16}$ fatty acid residue, wherein the at least one acryl-based polymer comprises at least one lipophilically modified acryl-based polymer, and wherein the polymeric ionic thick- ener cooperates with the non-ionic surfactant to stabilize and suspend the particulate material in the composition.

2. The water-based coloring cosmetic composition as set forth in claim 1, wherein the acryl-based polymer contains alkyl, aryl and/or alkaryl groups.

3. The water-based coloring cosmetic composition as set forth in claim 1, wherein it contains between 20 and 70% by weight of polymer.

4. The water-based coloring cosmetic composition as set forth in claim 1, wherein it contains between 40 and 60% by weight of polymer.

5. The water-based coloring cosmetic composition as set forth in claim 1, wherein it contains between 0.1 and 15% by weight of thickener.

6. The water-based coloring cosmetic composition as set forth in claim 1, wherein it contains between 0.2 and 0.5% by weight of thickener.

7. The water-based coloring cosmetic composition as set forth in claim 1, wherein the anionic or amphoteric-anionic surfactant is contained therein in an amount of between 0.2 and 3% by weight.

8. The water-based coloring cosmetic composition as set forth in claim 1, wherein the anionic or amphoteric-anionic surfactant is contained therein in an amount of between 0.3 and 1% by weight.

9. The water-based coloring cosmetic composition as set forth in claim 1, wherein the non-ionic surfactant is contained therein in an amount of between 0.2 and 3% by weight.

10. The water-based coloring cosmetic composition as set forth in claim 1, wherein the non-ionic surfactant is contained therein in an amount of between 0.3 and 1% by weight.

11. The water-based coloring cosmetic composition as set forth in claim 1, wherein between 0.1 and 50% by weight of pigments are included.

12. The water-based coloring cosmetic composition as set forth in claim 1, wherein between 5 and 16% by weight of pigments are included.

13. The water-based coloring cosmetic composition as set forth in claim 1, wherein the cosmetic composition additionally comprises one or more ingredients which are usual for cosmetic compositions selected from the group consisting of odiferous substances, vitamins, sun protection filters, moistening agents, perfumes, pH-regulators, aroma substances, anti-oxidants, preserving and care agents and mixtures thereof.

14. The water-based coloring cosmetic composition as set forth in claim 1, wherein the cosmetic composition is an eyebrow ink.

15. The water-based coloring cosmetic composition as set forth in claim 1, wherein the cosmetic composition ink is an eyeliner.

16. The water-based coloring cosmetic composition as set forth in claim 1, wherein the cosmetic is free of wax.

17. The water-based coloring cosmetic composition as set forth in claim 1, wherein the cosmetic is free of silicones/silicone resins.

18. The water-based coloring cosmetic composition as set forth in claim 1, wherein the particulate material is selected from the group consisting of talc, kaolin, starch, modified starch, polytetrafluoroethylene powder, nylon powder, boron nitride, insoluble metal soaps, inorganic pigments, organic pigments and mixtures thereof.

19. A water-based coloring cosmetic composition consisting essentially of at least one acryl-based polymer, at least one polymeric ionic thickener, at least one anionic or amphoteric-ionic surfactant, a particulate material, wherein the particulate material comprises a pigment and at least one non-ionic surfactant, wherein the non-ionic surfactant is a compound which contains between 4 and 8 units of PEG or PPG and a $C_8$ - $C_{16}$ fatty acid residue.

20. A water-based coloring cosmetic composition consisting essentially of at least one acryl-based polymer, at least one polymeric ionic thickener, at least one anionic or amphoteric-ionic surfactant, a particulate material, wherein the particulate material comprises a pigment and at least one non-ionic surfactant, wherein the non-ionic surfactant is a compound which contains between 4 and 8 units of PEG or PPG and a $C_8$ - $C_{16}$ fatty acid residue, wherein the at least one acryl-based polymer comprises at least one lipophilically modified acryl-based polymer, and wherein the polymeric ionic thickener cooperates with the non-ionic surfactant to stabilize and suspend the particulate material in the composition.

* * * * *